US011950069B2

(12) United States Patent
Ali

(10) Patent No.: US 11,950,069 B2
(45) Date of Patent: Apr. 2, 2024

(54) SYSTEMS AND METHODS FOR AUDIO SIGNAL EVALUATION AND ADJUSTMENT

(71) Applicant: Harman International Industries, Incorporated, Stamford, CT (US)

(72) Inventor: Hussnain Ali, Frisco, TX (US)

(73) Assignee: HARMAN INTERNATIONAL INDUSTRIES, INCORPORATED, Stamford, CT (US)

( * ) Notice: Subject to any disclaimer, the term of this patent is extended or adjusted under 35 U.S.C. 154(b) by 404 days.

(21) Appl. No.: 17/185,805

(22) Filed: Feb. 25, 2021

(65) Prior Publication Data

US 2021/0274283 A1    Sep. 2, 2021

Related U.S. Application Data

(60) Provisional application No. 62/982,628, filed on Feb. 27, 2020.

(51) Int. Cl.
*G06F 3/16* (2006.01)
*H04R 1/10* (2006.01)
*H04R 5/04* (2006.01)

(52) U.S. Cl.
CPC ............ *H04R 5/04* (2013.01); *G06F 3/165* (2013.01); *H04R 1/1091* (2013.01); *H04R 2420/01* (2013.01); *H04R 2430/01* (2013.01)

(58) Field of Classification Search
CPC .... H04R 5/04; H04R 1/1091; H04R 2420/01; H04R 2430/01; G06F 3/165
See application file for complete search history.

(56) References Cited

U.S. PATENT DOCUMENTS

| 9,681,246 | B2 | 6/2017 | Horbach |
| 9,918,177 | B2 | 3/2018 | Horbach |
| 10,104,485 | B2 | 10/2018 | Horbach |
| 2008/0159547 | A1 | 7/2008 | Schuler et al. |
| 2010/0135502 | A1 | 6/2010 | Keady et al. |

(Continued)

OTHER PUBLICATIONS

European Patent Office, Extended European Search Report Issued in Application No. 21150843.7, dated Jul. 12, 2021, Germany, 11 pages.

*Primary Examiner* — Joseph Saunders, Jr.
(74) *Attorney, Agent, or Firm* — McCoy Russell LLP

(57) ABSTRACT

Systems and methods are provided for monitoring auditory stimulation provided to a listener through a personal listening device. In one example, a method includes monitoring one or more acoustic profile parameters of an audio signal received from an audio source and rendered on a headphone assembly based on one or more received transducer parameters of one or more transducers of the headphone assembly; monitoring one or more listener-headphone engagement parameters based on headphone position data from a sensor coupled to the headphone assembly; and adjusting the audio signal and/or acoustic stimulation based on the monitoring of the one or more acoustic profile parameters and the monitoring of one or more listener-headphone engagement parameters, wherein the one or more listener-headphone engagement parameters include a current engagement status of the headphone assembly with respect to the user and a duration of active engagement of the headphone assembly with respect to the user.

18 Claims, 7 Drawing Sheets

(56) References Cited

U.S. PATENT DOCUMENTS

| | | | |
|---|---|---|---|
| 2011/0293129 A1* | 12/2011 | Dillen | H04S 7/304 |
| | | | 381/370 |
| 2013/0121494 A1 | 5/2013 | Johnston | |
| 2013/0279724 A1* | 10/2013 | Stafford | H04R 1/1041 |
| | | | 381/74 |
| 2013/0345842 A1* | 12/2013 | Karakaya | H04R 1/1041 |
| | | | 700/94 |
| 2017/0295445 A1 | 10/2017 | Christoph et al. | |

* cited by examiner

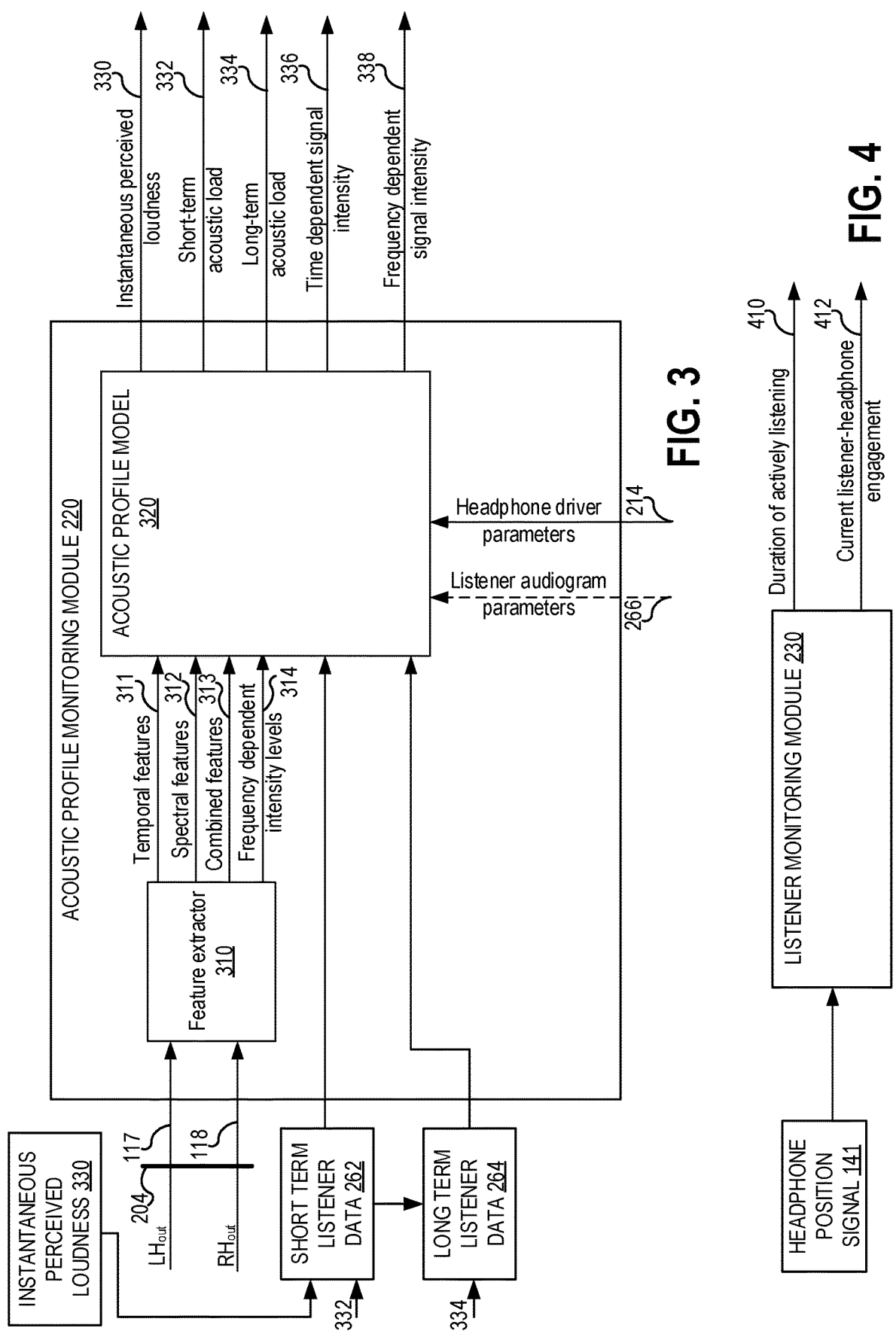

SYSTEMS AND METHODS FOR AUDIO SIGNAL EVALUATION AND ADJUSTMENT

CROSS REFERENCE TO RELATED APPLICATIONS

The present application claims priority to U.S. Provisional Application No. 62/982,628, entitled "SYSTEMS AND METHODS FOR AUDIO SIGNAL EVALUATION AND ADJUSTMENT", and filed on Feb. 27, 2020. The entire contents of the above-listed application are hereby incorporated by reference for all purposes.

TECHNICAL FIELD

The disclosure relates to systems and methods for evaluating acoustic stimulation perceived by a user, and adjusting audio signals delivered to the user based on the evaluation. Particularly, the disclosure relates to adjusting audio signals based on acoustic exposure and risk to the auditory health of the user.

BACKGROUND/SUMMARY

Noise-induced hearing degradation to human auditory systems, that is, hearing degradation caused by exposure to noise including listening to loud music from speakers/headphones/earbuds, etc., may be one of the leading causes of hearing degradation and other hearing problems, such as tinnitus. The louder a sound is, and the longer one listens to it, a degree of degradation to the auditory system is greater.

In general, the acoustic output of personal listening devices, such as headphones, earbuds, etc., may range from 75 decibels (dB) to as high as 136 dB. The maximum output levels may vary depending upon regulations and legislation in different countries. Typically, users of personal listening devices may choose to set the volume between 75 to 105 dB.

Systems and methods are provided herein for monitoring auditory stimulation provided to a listener through the personal listening devices, and providing one or more interventions and alerts to reduce the probability/potential of hearing degradation to the listener based on active monitoring.

In one embodiment, a method for an audio signal processor, comprises receiving an audio signal from an audio source; receiving a headphone position data from a sensor coupled to a headphone assembly rendering the audio signal to a user; receiving one or more transducer parameters from one or more transducers of the headphone assembly. The method further includes monitoring one or more acoustic profile parameters of the audio signal based on the one or more transducer parameters, monitoring one or more listener-headphone engagement parameters based on the headphone position data, and adjusting the audio signal and/or acoustic stimulation based on the monitoring of the one or more acoustic profile parameters and the monitoring of one or more listener-headphone engagement parameters, wherein the one or more listener-headphone engagement parameters include a current engagement status of the headphone assembly with respect to the user and a duration of active engagement of the headphone assembly with respect to the user.

In yet another embodiment, an audio rendering system, comprises a headphone assembly including a headband, a pair of headphones, each including one or more transducers, and one or more sensors coupled to each of the pair of headphones for sensing active headphone engagement with respect to a user; an audio evaluation system for monitoring auditory stimulation provided by an audio input rendered to the user via the headphone assembly. The audio evaluation system includes a controller with executable instructions stored in non-transitory memory for receiving the audio input signal from an audio source, receiving a headphone position data from the one or more sensors, receiving one or more transducer parameters from the headphone assembly, determining a first probability of short-term hearing degradation based on the audio input signal, the headphone position data, and the one or more transducer parameters, and adjusting the audio input signal prior to the headphone assembly rendering the audio input signal to the user based on the first probability of short-term hearing degradation.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The system may be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIG. 3 is a block diagram of an acoustic profile monitoring module of the acoustic evaluation system shown in FIG. 1, according to an embodiment of the present disclosure.

FIG. 4 is a block diagram of listener monitoring module of the acoustic evaluation system shown in FIG. 1, according to an embodiment of the present disclosure.

DETAILED DESCRIPTION OF THE DRAWINGS

Figure 1:
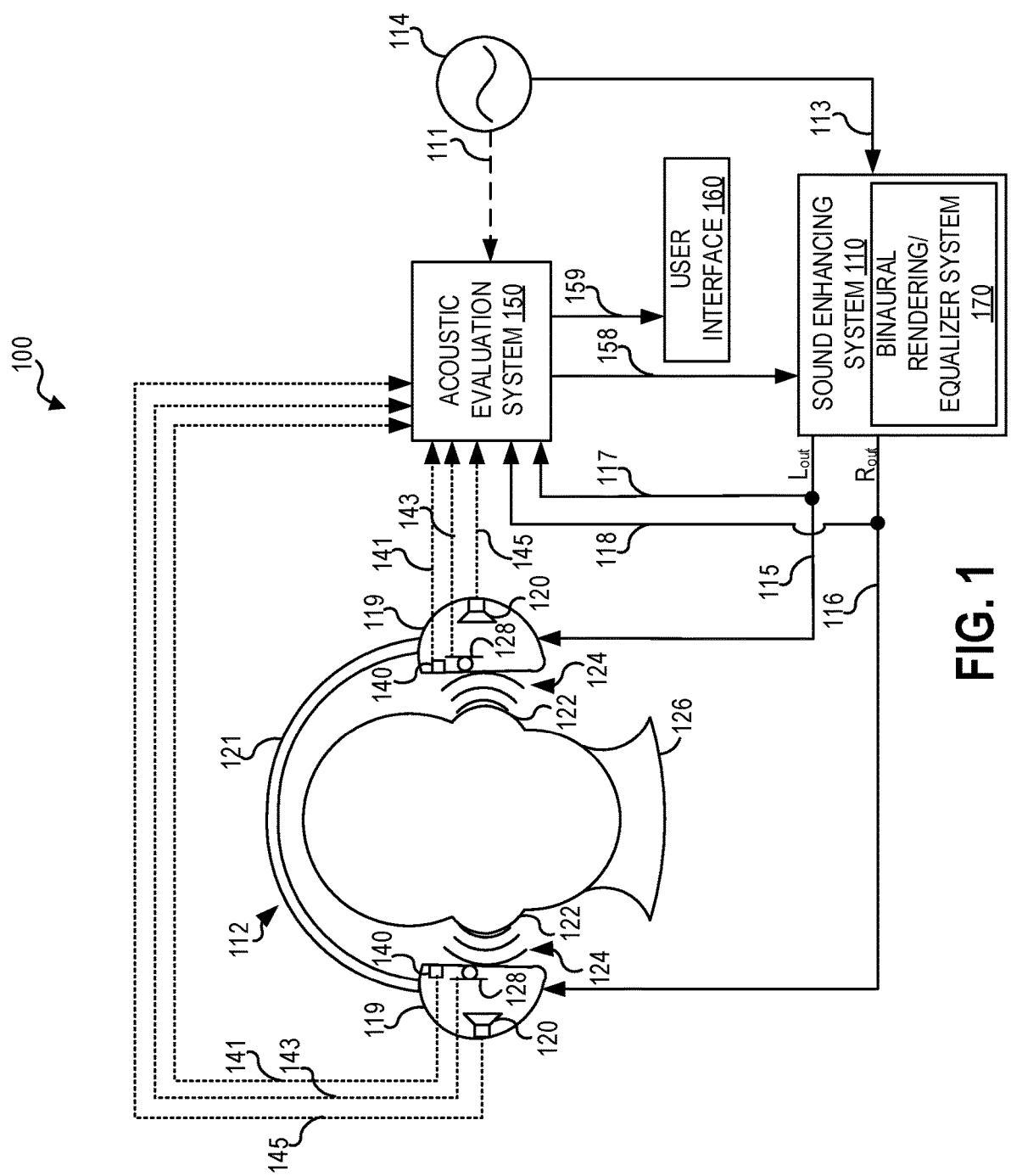
FIG. 1 is a schematic diagram illustrating an exemplary acoustic evaluation system connected to or embedded into a headphone assembly, according to an embodiment of the present disclosure.

With reference to FIG. 1, a sound system 100 for reproduction of sound is illustrated in accordance with one or more embodiments of the present disclosure. The sound system 100 may include a sound enhancing system (SES)

110 operatively coupled, via one or more of a wired and a wireless connection, to a headphone assembly 112. In some embodiments, the SES 110 may be integrated within the headphone assembly 112, such as in the headband 121 and/or one or more of the headphones 119.

The SES 110 may receive an audio input signal 113 from an audio source 114 and may provide audio output signal 115 to the headphone assembly 112. The audio signal may include audio content to be rendered for the headphones 112. The audio content may include digital audio formatted as multiple channels and/or objects (e.g., at least two channels or left and right stereo, 5.1 surround, and MPEG-4 Systems Specification). The digital audio may be in the form of a digital file that is stored locally (e.g., within a memory of a device playing the audio content) or a file that is streaming into the device from a server, over the Internet. The audio content may include, but is not limited to music, the soundtrack of a movie, radio content, podcast, the audio portion of live television (e.g., a sports event), an audiobook, and/or metadata of the audio signal/file.

The sound system 100 may include an acoustic evaluation system (AES) 150 for evaluating acoustic characteristics of the sound 124 rendered by the headphone assembly 112 and reaching the user's ears 122. The AES 150 may be operatively coupled to each of the SES 110 and the headphone assembly 112. The connection between the AES 150 and any of the SES 110 and the headphone assembly may be any of a wired or a wireless connection or a combination thereof. It will be appreciated that in some embodiments, the AES 150 may be included within the SES 110, and vice-versa. Further, in some other embodiments, the SES 110 and/or the AES 150 may be integrated into the headphone assembly 112. As an example, a digital signal processor of the headphone assembly 112 may be configured to implement one or more of the SES 110 and the AES 150. In still further embodiments, the AES 150 may be implemented by a controller of a computing device, via an application platform, for example, the computing device communicatively coupled (e.g., via a wired and/or a wireless connection) to the processor of the headphone assembly 112. The computing device may include the digital audio that is stored locally (e.g., within a memory of the computing device playing the audio content) and/or the audio file that is streaming into the device from the server. In some examples, the computing device may be a mobile computing device (e.g., a smartphone) that implements the AES and SES as an application.

The evaluation of the acoustic characteristics of the sound 124 reaching the user's ears 122 may include monitoring acoustic stimulation to the user 126 provided by one or more of the audio source 114 and the sound enhancing system 110, monitoring active listener engagement with the headphone assembly 112, inferring the effect of acoustic stimulation on ear health of the user 126 based on instantaneous, long-term, and short-term acoustic exposure, and providing one or more of alerts/indication to the user and automatic adjustments to the audio signal reaching the user's ears such that an average sound exposure level and/or acoustic frequencies likely to impact ear health to the user 126 are reduced.

The headphone assembly 112 may include the headband 121 and the pair of headphones 119. Each headphone 119 may include a transducer 120, or driver, that is positioned in proximity to a user's ear 122. The headphone assembly 112 may be positioned on top of a user's ears (supra-aural), surrounding a user's ears (circum-aural) or within the ear (intra-aural). The SES 110 provides audio output signals 115 and 116 to the headphone assembly 112, which are used to drive the transducers 120 to generate audible sound in the form of sound waves 124 to the user 126 wearing the headphone assembly 112.

The transducer 120 may output a signal 145 to the AES 150 indicating one or more parameters of the transducer 120 implemented with the headphone assembly 112. The one or more parameters may include a type of transducer, frequency response of the transducer, a power rating and consumption of the transducer, a maximum sound intensity generated by the transducer, transducer size, transducer mass, DC impedance, impedance vs frequency characteristics, sensitivity, resonant frequency, effective piston area, moving mass, motor force factor, voice coil diameter, voice coil inductance, mechanical quality (Q) factor, electrical quality (Q) factor, total quality (Q) factor, suspension compliance, efficiency factor, range of linear excursion, small signal lumped parameters of the transducer, transducer non-linear parameters, single-valued nonlinear parameters, electrical impedance including amplitude, and/or phase response. The parameters of the transducer and enclosure may include a quality factor of the enclosure, and coupling. Further, while the present example shows one transducer included within a headphone for an ear, it will be appreciated that the number of transducers and type of transducers may vary based on manufacturing specifications of the headphone assembly. Further, it will be appreciated that the AES 150 discussed herein may be implemented with regards to any type of personal listening device including, but not limited to, headphones, ear-buds, in-ear headphones, etc. In some embodiments, the AES 150 may be implemented for monitoring and adjusting sound output by any listening device, such as speakers, for example.

Each headphone 119 may also include one or more microphones 128 that are positioned between the transducer 120 and the ear 122. The microphones 128 may receive the environmental sounds, and a portion of the sound output by the transducer 120, and provide a reference audio input signal 143 to the AES 150. The reference audio input signal 143 may be a feedback signal indicating actual audio stimulation characteristics, which may be utilized by the AES 150 to evaluate one or more of a transducer operation and an AES operation based on deviation of a calculated audio stimulation characteristics from the perceived audio stimulation characteristics. In one example, the reference audio input signal 143 may indicate an actual perceived loudness of an instantaneous sound signal generated by the transducer 120, and the AES 150 may evaluate if a calculated perceived loudness based on signal input to the headphone assembly 120, which may be one or more of audio output signals 115, corresponding to left-channel audio output signal to headphone (Lout), and 116, corresponding to right-channel audio output signal to headphone (Rout), and audio source signal 114, is within a threshold deviation from the actual perceived loudness calculated based on transducer output signal received by the microphones 128. The difference between the actual perceived loudness and the calculated perceived loudness may be utilized to adjust one or more parameters of the AES, including one or more filter parameters, such that the difference is within the threshold.

Each headphone may further include a headphone position sensor 140 for monitoring user engagement (also referred to herein as listener engagement) with the headphone assembly. Specifically, the sensor 140 may be utilized to determine if the user is actively engaged in listening. The headphone position sensor 140 may output a signal 141 to the AES 150 that could be used to extract information on the level of contact of the headphone assembly 112 with the user's ears, and a duration of contact by the AES 150. The signal 141 may be utilized as input by the AES 150 to evaluate real-time acoustic characteristics of the sound stimulation provided to the user. The sensor 140 may be any of a capacitive sensor, a pressure sensor, and a temperature sensor, or any combination thereof, configured to provide an indication of whether the user's (that is, the listener's) ears are receiving acoustic stimulation and a duration of the stimulation.

The AES 150 may receive a plurality of inputs from each of the SES 110 and the headphone assembly 112, and may provide a plurality of output signals to each of the SES 110 and a user interface 160 of the sound assembly 100 based on the evaluation of the acoustic characteristics of the sound 124. The plurality of inputs may include input signals 141, 143, and 145 from each headphone 119 of the headphone assembly 112, and from the SES 110 output signals 117 (corresponding to left-channel audio output signal to AES 150) and 118 (corresponding to right-channel audio output signal to headphone). The plurality of outputs may include output signal 158 to the SES 110 and output signal 159 to the user interface 160. For example, based on the evaluation, the AES 150 may output signals to the SES 110 to adjust audio output signals 115 and 116 to the headphone assembly. The output signal 158 may include indications to filter-out or decrease an intensity of impulsive sounds, reduce overall acoustic intensity, adjust a spectral shape of the acoustic spectrum such that an amount of acoustic stimulation provided to the user does not increase above a threshold. In addition to instantaneous acoustic evaluation of the sound perceived by the user, short-term and long term listening characteristics of the user may be considered in evaluating the acoustic stimulation provided to the user by the headphone assembly, as further described below.

In one example, the user interface 160 may be a headphone user interface integrated with the headphone assembly 112, and the AES may provide output signals to the user interface 160 to provide one or more indications and alerts to the user and/or to a second user monitoring/observing the user 126. In another example, the user interface 160 may be a user interface of a computing device including one or more of the AES 150 and the SES 110. In some embodiments, the user interface 160 may be a user interface of a computing device communicatively coupled to the AES 150 and the SES 110. Further, in some embodiments, the AES 150 and the SES 110 may be integrated into a digital signal processor embedded within the headset assembly 112, and as such, the user interface 160 may be the user interface of the headphone assembly 112. In still further examples, the user interface 160 may be a mobile computing device (e.g., smartphone) application that acts as a feedback for the adjustments being performed by the SES 110 in real-time. The communication link (e.g., via which output signal 159 is carried) between AES 150 and the user interface 160 could be wired or wireless.

While the present example shows the AES 150 communicatively coupled to the headphone assembly 112 via the SES 110, it will be appreciated that the AES 150 may directly receive audio signals 111 from the audio source 114, receive a plurality of signals from the headphone assembly 112, and output a plurality of signals to directly to each of the headphone assembly 112 and the user interface 160 based on the evaluation of the acoustic characteristics of the audio signal.

In this way, by monitoring acoustic stimulation received by the user and active listener engagement with the headphone assembly, via the AES 150, the effect of instantaneous, short-term, and long-term acoustic stimulation may be inferred with the AES 150, based on which feedback to the user and/or audio stimulation adjustment may be provided via the AES 150, in order to reduce exposure to audio characteristics (e.g., overall intensity of the sound, peaks in the time-frequency domain, higher than average plateaus in the spectrum etc.), that are higher than maximum allowable daily noisy dose limits based on the exposure level for the user (e.g., which may be based on guidelines from one or more governing bodies, such as the CDC and/or NIOSH). Also, these thresholds/limits may be dynamically updated to keep track of overall acoustic exposure to the listener over time. In one example, AES 150 monitors listener engagement and characteristics of the acoustic stimulation over time to compute acoustic load (total dose of acoustic stimulation consumed by the listener or, said another way, cumulative acoustic exposure over a period of time). Based on the acoustic load, the threshold is updated over time. Depending on the dynamic characteristics of the acoustic stimulation, the threshold is updated based on a maximum allowable acoustic load for a period of time that could be a few hours or a day.

The SES 110 can enhance reproduction of sound emitted by the headphones 119. The SES 110 may improve sound reproduction by simulating a desired sound system having reduced unwanted artifacts typically associated with simulations of sound systems. The SES 110 facilitates such improvements by transforming sound system outputs through a set of one or more sum and/or cross filters, where such filters have been derived from a database of known direct and indirect head-related transfer functions (HRTFs), also known as ipsilateral and contralateral HRTFs, respectively. A head-related transfer function is a response that characterizes how an ear receives a sound from a point in space. A pair of HRTFs for two ears can be used to synthesize a binaural sound that seems to come from a particular point in space. For instance, the HRTFs may be designed to render sound sources in front of a listener at ±45 degrees.

In headphone implementations, eventually the audio output signal 115 of the SES 110 are direct and indirect HRTFs, and the SES 110 can transform any mono- or multi-channel audio input signal into a two-channel signal, such as a signal for the direct and indirect HRTFs. Also, this output can maintain stereo or surround sound enhancements and limit unwanted artifacts. For example, the SES 110 can transform an audio input signal, such as a signal for a 5.1 or 7.1 surround sound system, to a signal for headphones or another type of two-channel system. Further, the SES 110 can perform such a transformation while maintaining the enhancements of 5.1 or 7.1 surround sound and limiting unwanted amounts of artifacts.

The sound waves 124, if measured at the user 126, are representative of a respective direct HRTF and indirect HRTF produced by the SES 110. For the most part, the user 126 receives the sound waves 124 at each respective ear 122 by way of the headphones 119. The respective direct and indirect HRTFs that are produced from the SES 110 are specifically a result of one or more sum and/or cross filters of the SES 110, where the one or more sum and/or cross filters are derived from known direct and indirect HRTFs. These sum and/or cross filters, along with inter-aural delay filters, may be collectively referred to as binaural rendering filters.

In some embodiments, the headphone assembly 112 may also include a head-tracking sensor, such as a digital gyroscope (not shown). The head tracking sensor may be mounted on top of the headband 121. In one example, the heat tracking sensor may be mounted exactly between the headphones 119 on the headband 121. Alternatively, the sensor may be mounted in one of the headphones 119. By means of the head tracking sensor, the binaural rendering filters of the SES 110 may be updated in response to head rotation, via a feedback path, for example. The binaural rendering filters may be updated such that the resulting stereo image remains stable while turning the head. As a result, so-called "front-back confusion" may be reduced. In natural spatial hearing situations, a person performs mostly unconscious, spontaneous, small head movements to help with localizing sound. Including this effect in headphone reproduction may lead to improved three-dimensional audio experience with convincing out-of-the-head imaging.

The SES 110 may include a plurality of modules. The term "module" may be defined to include a plurality of executable modules. As described herein, the modules are defined to include software, hardware or some combination of hardware and software that is executable by a processor, such as a digital signal processor (DSP). Software modules may include instructions stored in memory that are executable by the processor or another processor. Hardware modules may include various devices, components, circuits, gates, circuit boards, and the like that are executable, directed, and/or controlled for performance by the processor.

Figure 2:
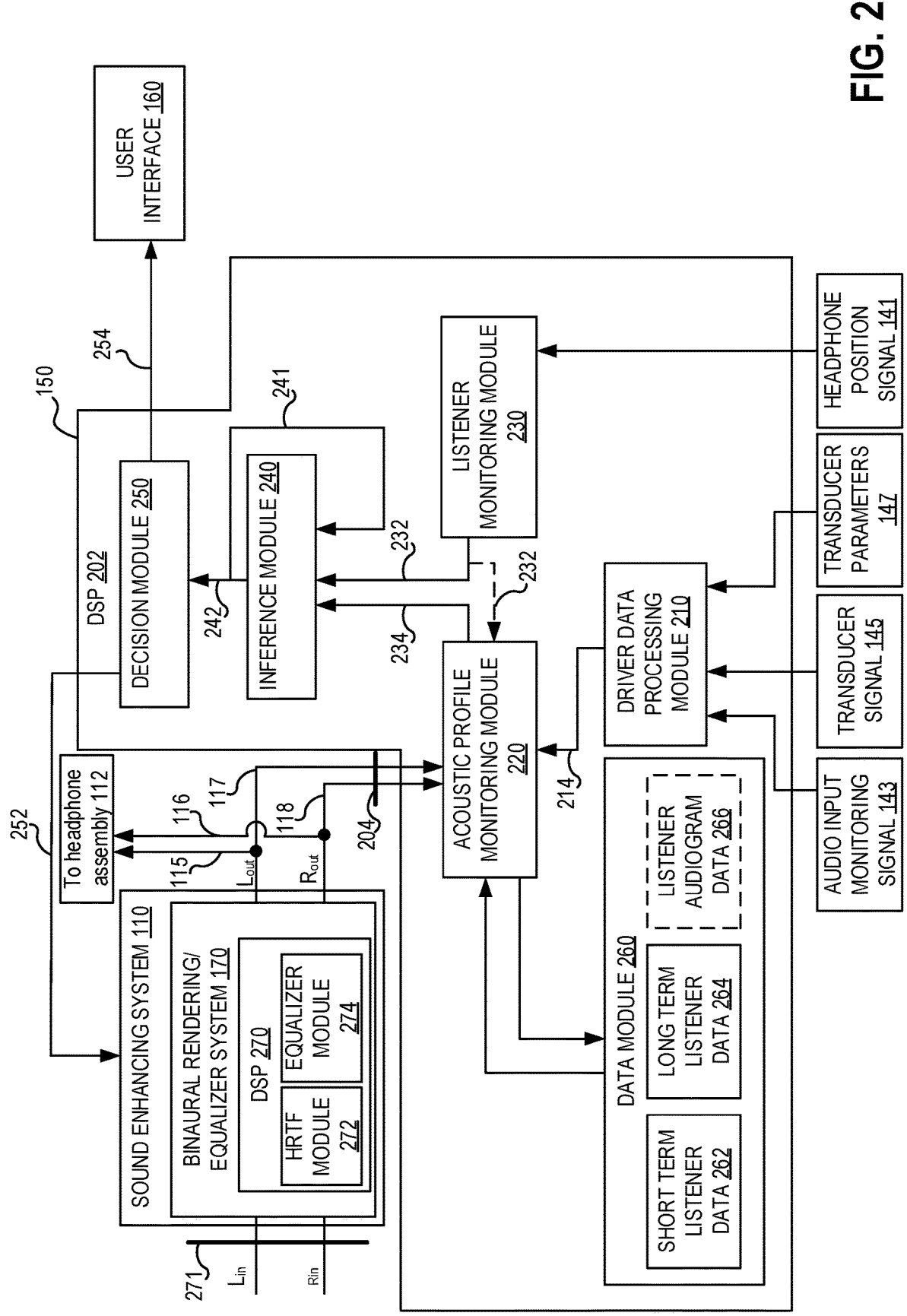
FIG. 2 is a block diagram of the acoustic evaluation system shown in FIG. 1, according to an embodiment of the present disclosure.

Next, FIG. 2 is a schematic block diagram of the AES 150. The AES 150 may include a digital signal processor (DSP) 202 and an audio signal interface 204. The audio signal interface 204 may receive the audio signals 117 and 118 from the SES 110, which may then be fed to the DSP 202. The audio signals 117 and 118 from the SES 110 correspond to a left-channel audio signal Lout and a right channel audio signal Rout respectively.

The DSP 202 may include an acoustic profile monitoring module 220 for monitoring characteristics of acoustic stimulation perceived by the user. The acoustic profile monitoring module 220 may receive audio signals 117 and 118, and may include executable instructions stored in a non-transitory memory to continuously monitor audio signals 117 and 118 from the SES 110. As discussed above, the Lout and Rout audio signals may drive one or more transducers, such as transducer 120 at FIG. 1, to generate audible sound in the form of sound waves to the user wearing a headphone assembly, such as headphone assembly 112 at FIG. 1. Thus, the audio signal that is used to drive the transducers to produce audible sound to the user wearing the headphone assembly is used as input to the acoustic profile monitoring module 220. In some embodiments, the acoustic profile monitoring module may receive audio signals from an audio source, such as audio signal 111 from source 114.

Further, the acoustic profile monitoring module 220 may receive one or more inputs from one or more sensors and transducers coupled to the headphone assembly. The one or more inputs may include the transducer signal 145 from the transducer within the headphone assembly, and the headphone position signal 141 from a headphone position sensor, such as sensor 40 at FIG. 1. The DSP 202 may include a driver data processing module 210 that processes one or more of the following: the transducer signal 145, an audio input monitoring signal 143, and transducer parameters 147. Specifically, these signals are processed to generate a digital signal 214 which is a driver-specific approximation of the acoustic stimulation delivered by the headphones. The digital signal 214 is then input into the acoustic profile monitoring module 220.

Further, the acoustic profile monitoring module 220 may be communicatively coupled to a data module 260 that stores short-term listener data 262 and long-term listener data 264. In some examples, the data module 260 may include listener audiogram data 266. The short-term listener data 262 may include a short-term profile of the acoustic load determined by the acoustic profile monitoring module 220 based on acoustic characteristics of the audio signals 117 and 118 over a short-term duration window on the order of few seconds to few minutes (e.g., 0-60 minutes). The long-term listener data 264 may include a long-term average acoustic load determined by the acoustic profile monitoring module 220 based on acoustic characteristics of the audio signals 117 and 118 over a long-term duration that is on the order of hours (e.g., 1 to 24 hours). Taken together, the acoustic profile monitoring module may determine short-term and long term data, and update the data module 260 based on the current audio data. While the present example shows data module 260 communicatively coupled to the acoustic profile monitoring module, examples where the data module 260 is implemented within (that is, the microcontroller and non-transitory memory of the data module is included in the acoustic profile monitoring module 220) the acoustic profile monitoring module 220 are also within the scope of the disclosure.

In some embodiments, an output 232 from a listener monitoring module 230, including one or more listener engagement parameters, may be input into the acoustic profile monitoring module 220. In this case, the short-term listener data 262 may include the short-term profile of the acoustic load determined by the acoustic profile monitoring module 220 based on acoustic characteristics of the audio signals 117 and 118 over the short-term duration window and listener engagement parameters over the short-term window duration. Similarly, the long-term listener data 264 may include the long-term average acoustic load determined by the acoustic profile monitoring module 220 based on acoustic characteristics of the audio signals 117 and 118 over a long-term duration and listener engagement parameters over the long-term window duration.

Further, the acoustic profile monitoring module 220 may output a signal 234 that includes an instantaneous actual perceived loudness, the short-term acoustic load, and the long-term average acoustic load. Further, in some examples, the acoustic profile monitoring module 220 may utilize the listener's audiogram data 266 to adjust the instantaneous perceived loudness, short-term acoustic load and the long-term acoustic load that is customized based on the user. For example, for the same audio signal and listener engagement parameters, the instantaneous loudness, short-term acoustic load, and the long-term average acoustic load may be different for a user with hearing loss than for a user with normal auditory function. Further, the signal 234 may include a time dependent signal intensity and a frequency dependent signal intensity. As used herein, "acoustic load" may refer to a metric describing transformation of the acoustic stimulation from physical sound waves to physiological loudness percept in a specific period of time. For example, the acoustic load may keep growing the longer one is exposed to acoustic stimulation, and the higher the sound intensity, the faster is the rate at which acoustic load grows. In this way, acoustic load may be considered as a cumulative acoustic exposure.

The listener monitoring module 230 may monitor listener engagement with the headphone assembly. Specifically, the listener monitoring module 230 may actively monitor active engagement of the user during a listening process. In particular, the listener monitoring module 230 may determine if the user is utilizing the headphone assembly and listening through the headphone assembly. Further, the listener monitoring module may track a duration of total listening, a number of breaks taken by the user during the listening process, and respective durations of the breaks.

The listener monitoring module 230 may receive input regarding headphone position to determine active user engagement with the headphone assembly. In particular, the listener monitoring module 230 may receive a headphone position signal 141 from one or more sensors coupled to the headphone assembly, such as sensor 140, for determining if the headphone is positioned with respect to a user's anatomy (e.g., ears) such that the user is listening through the headphone assembly. The listener monitoring module 230 may process sensor data (that is the headphone position data) to provide output 232 that includes one or more listener monitoring parameters including a level of contact of the headphone assembly with the user and a duration of contact.

The DSP 202 further includes an inference module 240 for determining one or more of a short-term hearing impact and long-term hearing impact for the user based on the acoustic profile of the audio signal, determined by the acoustic profile monitoring module 220, and the listener engagement 230, determined by the listener monitoring module, with the headphone assembly. Thus, the inference module 240 may receive, as inputs, the signal 234 output from the acoustic profile monitoring module 220 that includes the instantaneous actual perceived loudness, the short-term acoustic load profile, and the long-term average acoustic load, and output 232 from the listener monitoring module 230 that includes one or more listener engagement parameters.

The inference module 240 may provide an output 242 that includes a probability of short-term hearing impact and a probability of long-term hearing impact. The output 242 may be provided as feedback to the inference module 240 to actively adjust the short-term and the long-term hearing impact.

The DSP 202 further includes a decision module 250 that takes the output 242 from the inference module to determine one or more of an initiation time point for intervention, a duration of intervention, and a type of intervention. The decision module 250 may provide a first output 252 that includes one or more intervention parameters and a second output 254 that includes one or more alerts and indications.

The one or more intervention parameters may include identification of impulsive sounds in the incoming audio signal, an amount and duration of decrease in intensity for the impulsive sounds, an amount and duration of decrease of overall intensity, and adaptive spectral shaping parameters. The first output 252 including the one or more intervention parameters may be input into the SES 110 for adjusting the sound signals that are subsequently input into the headphone assembly and delivered to the user via the headphone assembly.

Figure 7:
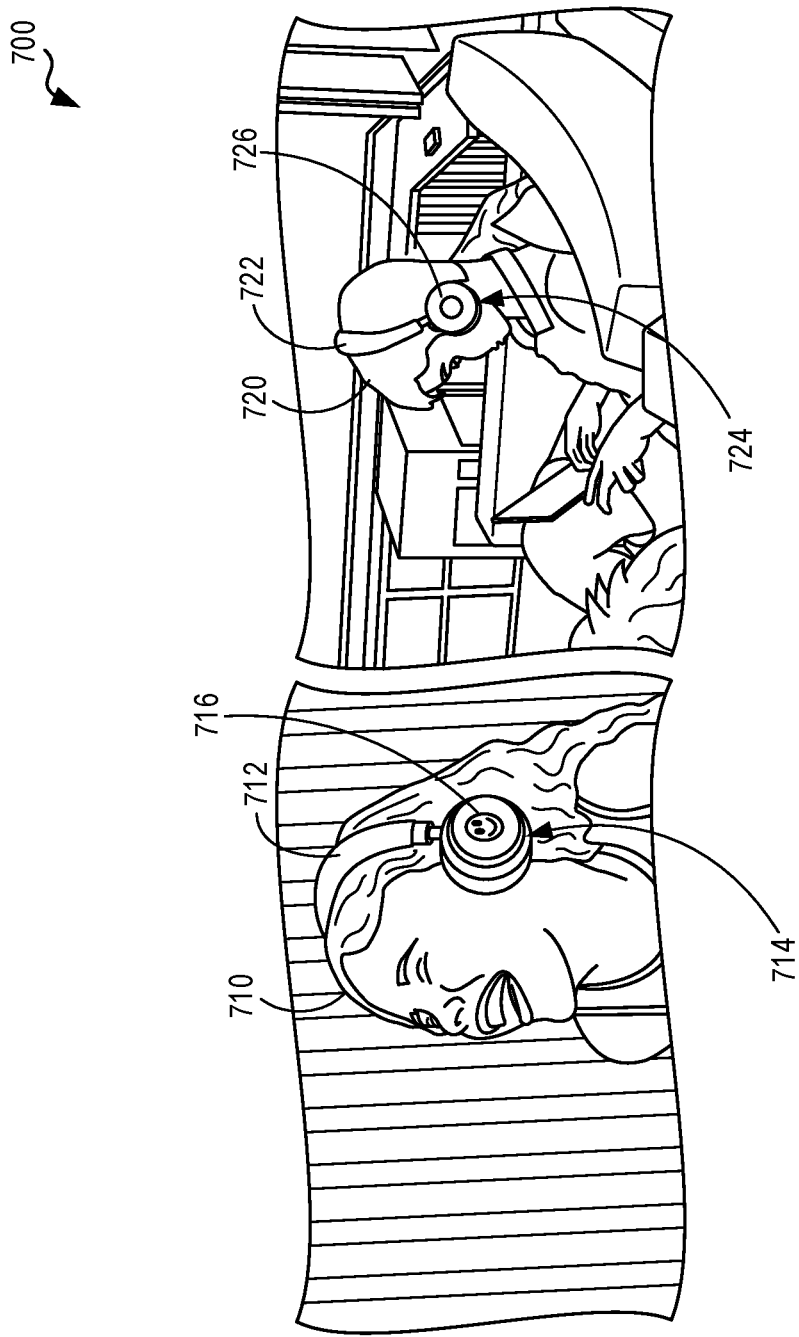
FIG. 7 shows a first exemplary indication and a second exemplary alert provided through a first and second headphone user interfaces respectively, according to one or more embodiments of the present disclosure.

The one or more alerts and indications may include an indication of expected impact to hearing including a duration and intensity to reach the expected impact. The second output 254 including the one or more alerts and indications may be provided to the user interface 160. Thus, the one or more alerts and indications may be based on the type of user interface. In one example, the one or more alerts and indications may be one or more of a voice alert, a visual alert, and a haptic alert. An example alert provided via a headphone user interface is illustrated at FIG. 7.

The SES 110 may include an audio signal interface 271 and a DSP 270. The audio signal interface 271 may receive the audio input signal 113 from the audio source 114, which may then be fed to the DSP 270. The audio input signal 113 may be a two-channel stereo signal having a left-channel audio input signal Lin and a right channel audio input signal Rin. A pair of parametric models of head-related transfer functions (HRTF) may be implemented via a HRTF module 272 in the DSP 271 to generate a left headphone output signal LH and right headphone output signal RH. Further, the DSP 271 may include an equalization module 274 including one or more filters for improving the perceived spectral balance based on headphone type and construction. As previously explained, a HRTF is a response that characterizes how an ear receives a sound from a point in space. A pair of HRTFs for two ears can be used to synthesize a binaural sound that seems to come from a particular point in space. For instance, the HRTFs (e.g., implemented via the HRTF module 272) may be designed to render sound sources in front of the listener (e.g., at ±30 degrees or ±45 degrees relative to the listener).

The SES 110 receives output 252 from the AES 150, and may adjust one or more parameters of the SES 110 based on the output 252 to adjust output audio signals 115 and 116 to the headphone assembly 112.

Turning to FIG. 3, a block diagram of an acoustic profile monitoring module, such as the module 220 at FIG. 2, is shown. As discussed above, the acoustic profile monitoring module 220 may be implemented to monitor instantaneous, short-term, and long-term acoustic stimulation provided via a listening device, such as headphone assembly 112 at FIG. 1.

The acoustic profile monitoring module 220 may include a feature extractor 310 for extracting one or more temporal features 311, spectral features 312, overall frequency-dependent intensity levels 314, and combined temporal+spectral features 313 from the audio signals input into the acoustic profile monitoring module 220. These include family of temporal/spectral features such as linear predictive coding (LPC) coefficients, MEL-frequency cepstral coefficients (MFCC), Short-Time Fourier Transform (STFT), and Wavelet decomposition features. The audio signals may be received via the audio interface 204. In one example, the audio signals may include a left-channel audio signal 117 and a right-channel audio signal 118, each output from a sound enhancement system, such as SES 110 at FIG. 1. In another example, the audio signal may be obtained from any source, such as audio source 114 at FIG. 1.

Further, in addition to the audio signal, the acoustic profile monitoring module 220 may receive as input short term listener data 262 and long term listener data 264. Furthermore, headphone driver/transducer parameters, such as signal 214 from a driver data processing module 210 as discussed at FIG. 2, may be input into the acoustic profile monitoring module 220.

The acoustic profile monitoring module 220 includes an acoustic profile model 320 that comprises of a signal processing chain, a machine learning algorithm, or a hybrid of both that receives the extracted features 311, 312, 313, and 314, short-term listener data 262, long-term listener data 264, and transducer parameters 214 to generate an instantaneous perceived loudness 330, a profile of short-term acoustic load 332, an average long-term acoustic load 334, a time dependent average signal intensity 336 (e.g., a measure of energy intrinsic in the signal), and a frequency dependent signal intensity 338. One embodiment of the acoustic profile model 320 is a neural network that is comprised of an input layer that takes input features 311, 312, 313, 314, one or more hidden layers that establish relationship(s) between the input and output layers, and an output layer that comprises of output parameters 330, 332, 334, 336, and 338. The network may be trained experimentally with a test data to compute the number of nodes, number of layers, and weights of each link/connection between the layers/nodes. The trained network, which may be a deep neural network, is able to take in input features and compute output parameters. In another embodiment, the acoustic profile model is a transformation between input vectors and output vectors. For example, the combined features 313 (which may be average RMS features) may be mapped to the perceived instantaneous loudness 330 using a mathematical non-linear transformation. This may take into account a listener's audiogram data to compute an accurate representation of perceptual loudness.

Further, the instantaneous perceived loudness 330 may be provided as feedback into the model 320. For example, the instantaneous perceived loudness 330 may be provided as feedback to the short-term listener data 262. Further, the short-term acoustic load 332 may also be provided as feedback to the short-term listener data 262. The long-term acoustic load 334 may be provided as feedback to the long-term listener data 264.

Next, FIG. 4 shows a block diagram of a listener monitoring module 230. As discussed above, the listener monitoring module 230 may receive a sensor input from headphone 112, such as the headphone position signal 141 from headphone position sensor 140 at FIG. 1. The listener monitoring module 230 may process the headphone position signal 141 and provide one or more outputs including a current state of listener headphone engagement 412 and a current duration of active listening 410. Further details of determining the current duration of active listening and the current state of headphone engagement is discussed below at FIG. 8.

Figure 8:
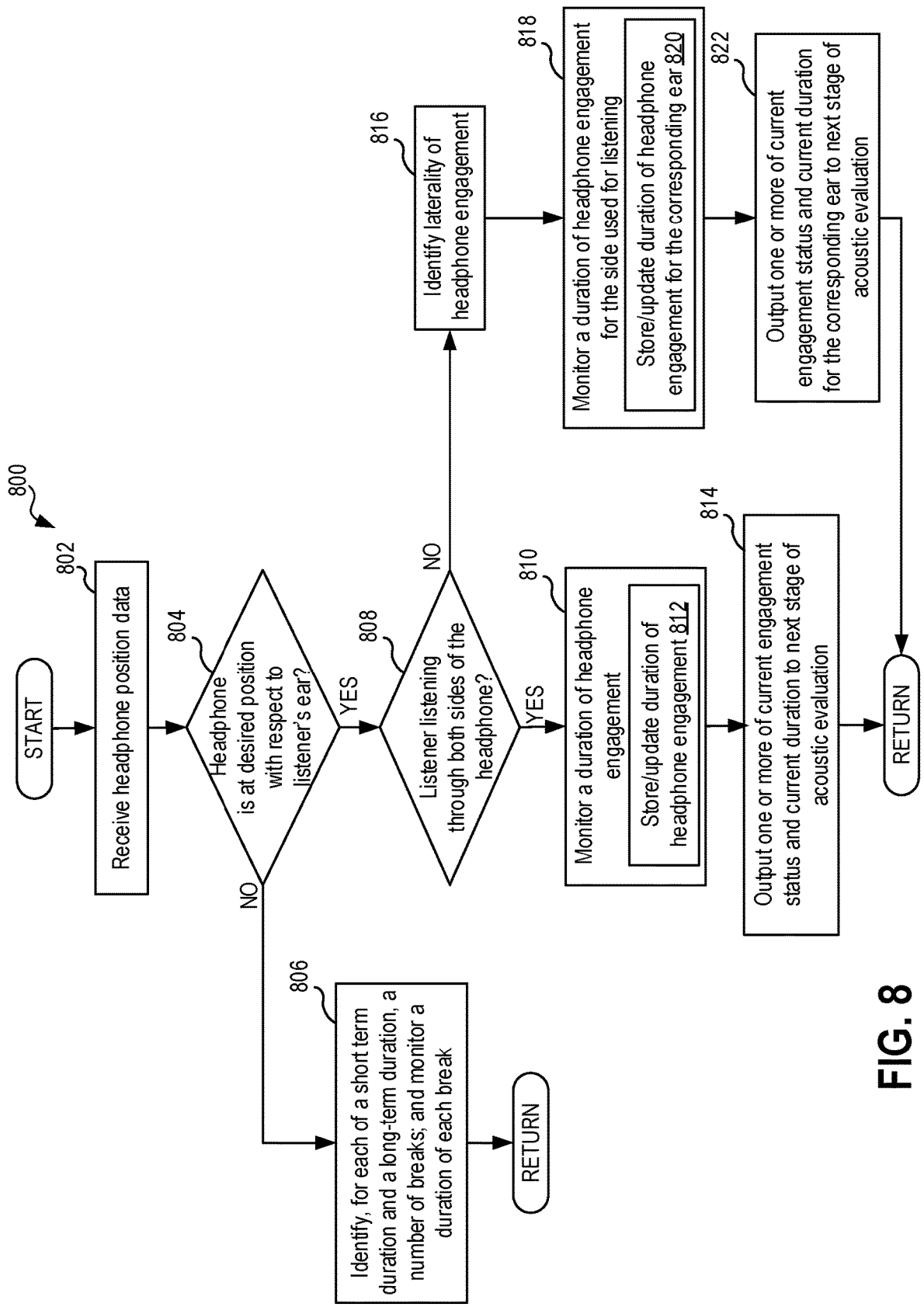
FIG. 8 is a high-level flowchart illustrating an exemplary method for determining one or more listener monitoring parameters, according to an embodiment of the present disclosure.

Turning to FIG. 8, a high level flowchart illustrating an example method 800 for determining the current duration of active listening and the current state of headphone engagement is shown. The method 800 may be implemented based on instructions stored in non-transitory memory, such as a non-transitory memory of a processor of the listener monitoring module 230 described at FIG. 2, a digital signal processor of an audio evaluation system, such as DSP 202 at FIG. 2, a digital signal processor of a sound enhancement system, such as DSP 270 at FIG. 2, an edge device connected to the sound enhancement system and/or the audio evaluation system (which may include a smartphone, smartwatch, smartglasses, or other suitable device), a cloud in communication with the sound enhancement system and/or the audio evaluation system, any sound processing system of a listening device, such as headphone 112 at FIG. 1, or any appropriate combination thereof. The method 800 may be initiated in response to active sound produced via the listening device (that is, the headphone 112) to determine if one or more of the listener's ears are actively stimulated by the audio produced by the listening device, and further determine one or more parameters of the listening process as further discussed below.

Method 800 begins at 802. At 802, the method 800 includes receiving a headphone position signal from one or more sensors coupled to the headphone. The headphone position signal may include headphone sensor data from one or more headphone position sensors coupled to the headphone, such as sensor 140 at FIG. 1.

Next, at 804, the method 800 may determine if the headphone is at desired position with respect to the listener's ear based on the headphone sensor data. Specifically, the method 800 may determine if the listener is actively listening via the headphone based on whether the headphone is positioned at the desired position for active listening with respect to the listener's ear. The desired position may depend on the type of headphone used. For example, for an over-the-ear headphone, when the headphone is producing audio output (via transducers/drivers), if the listener has placed the headphones around their neck, the headphone is not at the desired position for active listening. Accordingly, the method 800 may determine that the listener is not actively listening through the headphone even through audio output is generated by the headphone and the listener is in contact with the headphone (around the neck). Thus, determining if the headphone is at the desired position may include determining a current position of the headphone with respect the listener. The current position may be determined based on signal output by one or more headphone position sensors and the type of sensor used. For example, if a pressure-based sensor is used, a contact pressure between the headphone and the user when the headphone is positioned on the ear may be different (greater) from a contact pressure when the headphone is positioned around the neck or a different body part/clothing, since a level of contact may be different. As another example, if a temperature-based sensor is used, a temperature sensed by a surface of the headphone touching the listener's ear may be different from a temperature sensed when the surface is touching a different body part other than the ear and/or touching clothing. As another example, a capacitive sensor will generate different voltage levels for in-contact with the body and out-of-contact with the body. This combined with an optical sensor and a vital sign monitoring sensor (e.g., blood flow, $SpO_2$), may be used to determine the level of contact with the body. While the above examples discuss pressure, temperature, optical, and physiological sensors, it will be appreciated that any other type of sensor or combinations thereof for determining active listener engagement may be used. In some examples, a threshold range may be established for active-listening conditions, and when the sensor signal is outside the threshold range, it may be determined that the headphone is not at the desired position with respect to the listener's ear.

If it is determined that the headphone is not at the desired position, the method 800 proceeds to 806. At 806, the method 800 may identify that there is a break in active listening, and for each of a short-term duration and a long-term duration, a number of such breaks may be identified. Further, a duration of each break (determined via a counter, for example) during each of the short-term duration and the long-term duration may be monitored and stored. The method 800 then returns.

If the headphone is at the desired position, the method 800 proceeds to 808. At 808, the method 800 may determine if the listener is actively listening through both the channels/sides (that is left channel and right channel) of the headphone based on the sensor data. For example, if a position sensor is arranged on a headband, then the position sensor may be oriented differently for a user listening with both ears, only a left ear, or only a right ear. If the position sensor is arranged in each headphone, then feedback from the position sensors may be compared, and if there is a difference in the feedback, then the use may be using only one headphone to listen to music. Additionally or alternatively, if the position sensor indicates a high amount of movement of only one headphone while the other headphone is relatively stationary, then it may be determined that only one headphone is being use to listen to audio. If YES, the method 800 proceeds to 810. At 810, the method 800 may monitor a current duration of headphone engagement from a time point the headphone was at the desired position, and as indicated at 812, the method 800 may store and constantly update the current duration of headphone engagement.

Next, at 814, the method 800 may output the current engagement status, which may include an indication that the listener is actively listening through both the ears, to a next stage of an acoustic evaluation algorithm (e.g., to inference module 240 at FIG. 2). Further, the method 800 may output the current duration of active listening to the next stage of the acoustic evaluation algorithm. The method 800 then returns.

Returning to 808, if the listener is listening through only one channel, the answer at 808 is NO, and the method 800 proceeds to 816. At 816, the method 800 may identify a laterality of active listening based on headphone position data. Identifying the laterality may include identifying the corresponding ear through which the listener is actively listening. Identification of laterality may be based on relative positions of each the headphones (left and right) with respect to the listener's ear, and a head orientation of the listener, for example. Upon identifying laterality of headphone engagement, the method 800 proceeds to 818.

At 818, the method 800 may monitor a current duration of headphone engagement from a time point the headphone was at the desired position for the corresponding ear, and as indicated at 820, the method 800 may store and constantly update the current duration of headphone engagement for the corresponding ear.

Next, similar to step 814, at 822, the method 800 may output the current engagement status for the corresponding ear, which may include an indication that the listener is actively listening through one ear, to a next stage of an acoustic evaluation algorithm (e.g., to inference module 240 at FIG. 2). Further, the method 800 may output the current duration of active listening or the corresponding ear to the next stage of the acoustic evaluation algorithm. The method 800 then returns.

In this way, listener engagement with the headphone may be actively monitored by the listener monitoring module based on input from the headphone position sensors.

Figure 5:
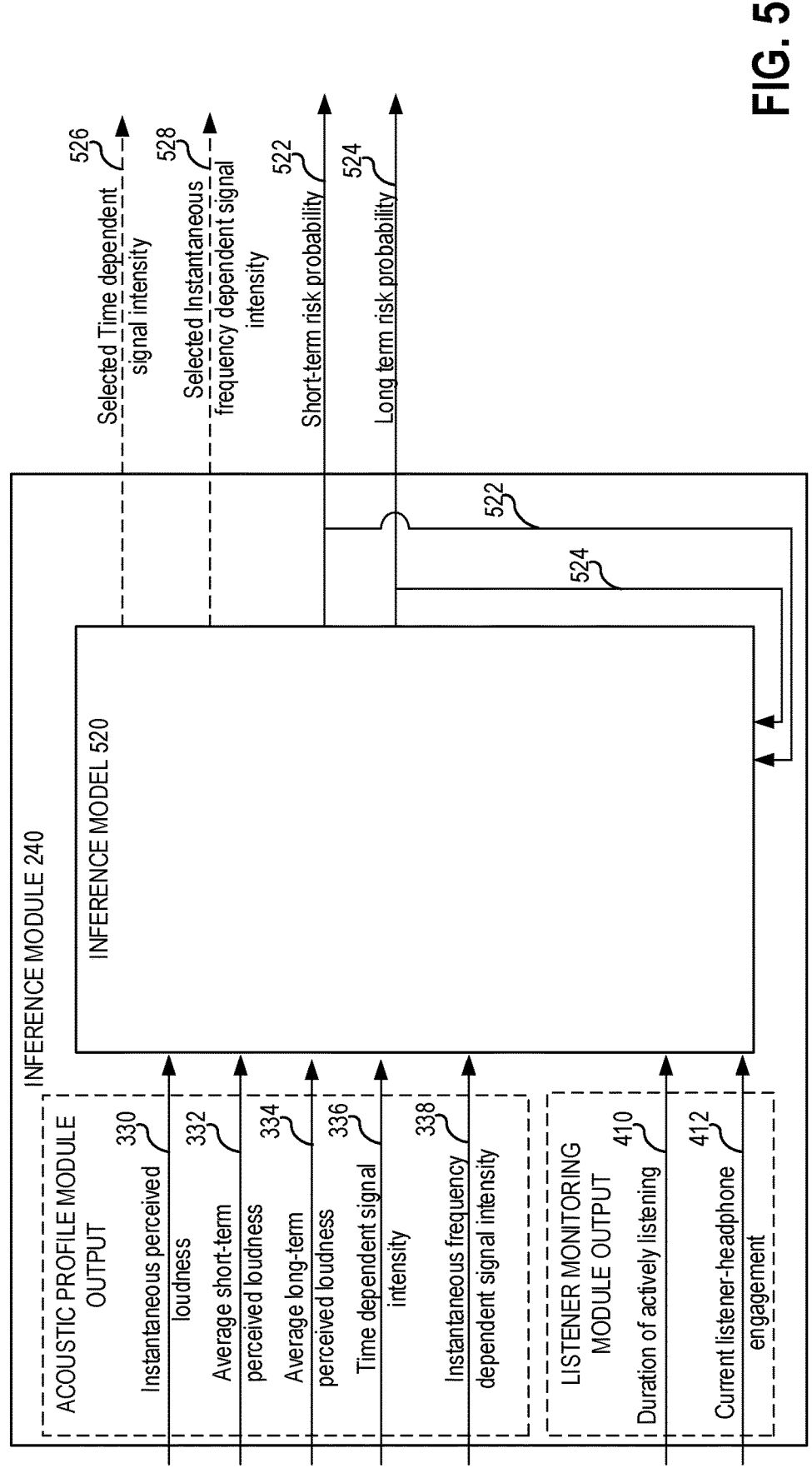
FIG. 5 is a block diagram of an inference module of the acoustic evaluation system shown in FIG. 1, according to an embodiment of the present disclosure.

Turning next to FIG. 5, a block diagram of the inference module 240 is illustrated. As shown, the inference module 240 may implement an inference model 520 that receives inputs from the acoustic profile monitoring module 220 and listener monitoring module 230. In particular, the inference model 520 may receive a plurality of inputs from the acoustic profile monitoring module 220 including the instantaneous perceived loudness 330, the short-term acoustic load profile 332, the average long-term acoustic load 334, the time dependent signal intensity 336, and the instantaneous frequency dependent signal intensity 338. The inference model 520 may further receive a plurality of inputs from the listener monitoring module 230 including the current duration of active listening 410 and the current listener-headphone engagement status 412.

The inference model 520 may utilize the plurality of inputs from the modules 220 and 230, and determine a short-term risk probability 522 and a long-term risk probability 524 for a listener actively using the headphone assembly 112. The inference model 520 may also receive feedback from previous short-term and long-term probability outputs to update the short-term probability 522 and the long-term probability 524. Details of determining the short-term risk probability and the long-term risk probability using the inference model will be further described below The inference engine is a neural network that is comprised of an input layer that takes plurality of inputs, one or more hidden layers that establish relationship between input and output layers, and an output layer that comprises of short-term and long-term probabilities of risk to the auditory health. The network is trained experimentally with a test data to compute the number of nodes, number of layers, and weights of each link. The trained network, which may be a deep neural network, is able to take in input features and compute output probabilities. In another embodiment, the acoustic profile model is a purely fuzzy inference system or an adaptive neuro-fuzzy inference system that processes inputs based on the pre-specified rules to produce the outputs. One example of a possible classification rule may be that if the instantaneous perceived loudness is beyond a predetermined threshold, the short-term risk probability is high or close to 1. In another example, if the duration of active listening is large and listener headphone engagement is active and inputs from the acoustic profile monitor are towards the ceiling end, the short-term and long-term probabilities of auditory risk are large. In another example, if the output of the listener monitoring module is low, then the short-term and long-term probabilities of auditory risk are low indicating no active listening, no matter what the output from the acoustic profile module is. The input-output mapping relationships/strategy may be modeled via one or more machine learning approaches such as support vector machines, artificial neural networks, K-Means, etc.

Further, the inference model 520 may identify selected time dependent signal intensities and frequency dependent signal intensities from the time dependent signal intensity 336 and frequency dependent signal intensity 338 to identify one or more impulse sounds in the audio sequence. The inference model 520 may output one or more selected time dependent signal intensities 526 and one or more selected frequency dependent signal intensities 528 that correspond to one or more impulsive sounds in the audio sequence. Further, one or more audio windows in the input audio sequence when signals 526 and 528 are present may be identified.

Figure 6:
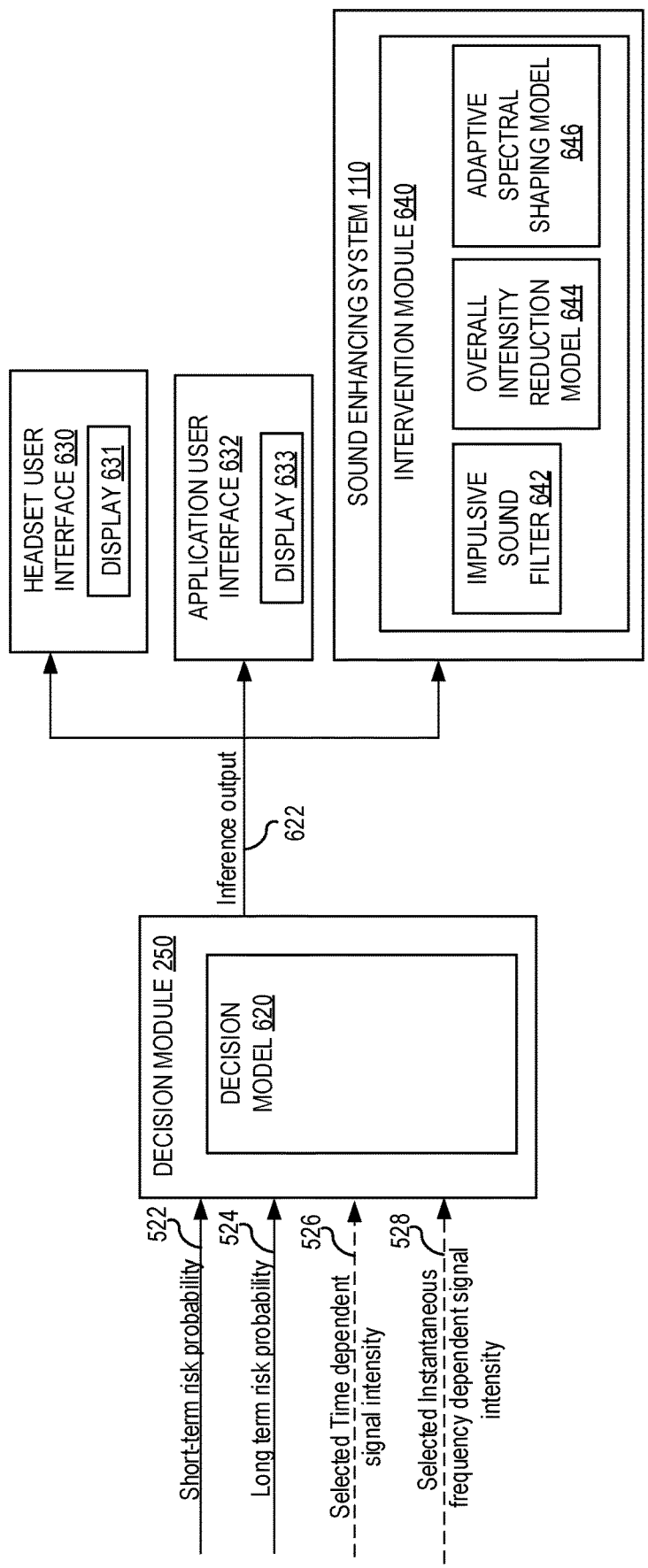
FIG. 6 is a block diagram of a decision module of the acoustic evaluation system shown in FIG. 1, according to an embodiment of the present disclosure.

The short-term and long-term probability outputs 522 and 524 may be subsequently input into a decision module, such as decision module 250 at FIG. 2, further described at FIG. 6. Turning to FIG. 6, a block-diagram of the decision module 250 is shown. The decision module 250 may be utilized to determine if an intervention to reduce degradation to a listener's hearing capability is needed, and further determine a type of intervention that may be provided. The decision module 250 may implement a decision model 620 that takes into account the short-term risk probability and the long-term risk probability, and provides an inference output 622.

The decision model 620 may evaluate the short-term risk probability 522 with respect to a short-term threshold, evaluate the long-term risk probability 524 with respect to a long-term threshold, and determine if an intervention is needed to reduce degradation of hearing to the listener currently actively listening through the headphone. Further, depending on one or more of the short-term risk probability and the long-term risk probability, the decision model 620 may determine a type of intervention. As an example, guidelines from the CDC and/or NIOSH may provide a basis for the thresholds discussed above, such as a short-term threshold of 90-100 dB and a long-term threshold of 80-85 dB.

Further, in some examples, the decision model 620 may compare the one or more selected time dependent signal intensities 526 with respect to a first intensity threshold, and compare the one or more selected frequency dependent signal intensities 528 with respect to a second intensity threshold to determine the type of intervention.

The inference output 622 provided by the decision model 620 may include an indication of requirement for intervention, and indication of one or more types of intervention. The types of interventions may include alerts/notifications, filtering of impulsive sounds, overall intensity reduction, and/or frequency-dependent spectral shaping of the acoustic spectrum. The type of intervention applied may depend on the short-term risk probability and the long-term risk probability, e.g., one type of intervention may be applied when the short-term risk probability reaches the short-term threshold while another type of intervention may be applied when the long-term risk probability reaches the long-term threshold.

The inference output 622 is then provided to a headset user interface 630 including a display portion 631 for providing an indication to the listener and/or an observer of the listener regarding one or more of a potential short-term degradation and a potential long-term degradation. The indication to the listener and/or the observer may be one or more of a visual indication, an audible indication, and a haptic indication. For example, a visual light or an emoticon-based indication may be provided via a display portion 631 of the user interface 630. Exemplary visual indications provided to the listener and/or observer on exemplary headset user interfaces are shown at FIG. 7.

Turning to FIG. 7, exemplary set 700 of images including a first headphone assembly 712 utilized by a first user 710 and a second headphone assembly 722 utilized by a second user 722 are shown. The first headphone assembly 712 includes a first headphone user interface including a display portion 714, and the second headphone assembly 722 includes a second headphone user interface including a display portion 724. The display portions 714 and 724 may be examples of display portion 631 of headset user interface 630 at FIG. 6.

During active listening by the first user 710, the headphone assembly 712 produces and delivers audio to the ears of the first user 710. Similarly, during active listening by the second user 720, the headphone assembly 722 produces and delivers audio to the ears of the second user 720.

Looking to the first headphone assembly 712, a first acoustic evaluation system of the headphone assembly 712, such as the AES 150 at FIG. 1, may determine that the short-term risk probability and the long-term risk probability for the first user 710 are within respective thresholds, and as such a visual indication 716, such as a green light signal and/or a first emoticon, indicating that the user's listening is below limits for short-term risk and long-term risk may be provided via the first display portion 714.

Turning to the second headphone assembly 722, a second acoustic evaluation system of the second headphone assembly 722, such as the AES 150 at FIG. 1, may determine that one or more of the second short-term risk probability and the second long-term risk probability or the second user 720 are not within respective thresholds, and as such a visual indication 726, for example, a red light signal and/or a second emoticon, indicating that the user's listening is above the limits for one or more of short-term risk and long-term risk may be provided via the second display portion 724. It is to be understood that the display light colors and emoticons provided in FIG. 7 are exemplary, and other mechanisms for indicating the listener's short-term and/or long-term risk probabilities are within the scope of this disclosure, such as thumbs up/thumbs down, text notifications, etc.

Returning to FIG. 6, the inference output 622 is further provided to an application user interface 632 having a display portion 633. The application user interface 632 may be included on a computing device including at least a processor and non-transitory memory communicatively coupled to one or more of the sound enhancing system, such as SES 110 at FIG. 1, and the acoustic evaluation system, such as AES 150 at FIG. 1. The computing device may be utilized by the listener to select an audio source for rendering via the headphones, for example. Depending on the short-term and the long-term risk probabilities, one or more visual, audible, and haptic indications may be provided to the listener and/or the observer via the user interface 632.

Further, the inference output 622 may be provided to an intervention module 640. In one example, the intervention module 640 may be included in the acoustic evaluation system 150. In another example, the intervention module 640 may be included in the sound enhancing system 110, as shown herein.

Impulsive sounds may include short duration, high intensity sounds, such as a sound produced by a thunder storm. Impulsive sounds above a threshold intensity e.g., close to 100 decibels sound pressure level, appearing at random portions in the audio sequence can increase the risk of permanently damaging the hearing several folds. Thus, the intervention module 640 may include an impulsive sound filter 642 for reducing impulsive sounds in the audio sequence rendered via the headphones. The impulsive sound filter 642 may receive inference output 622 that includes one or more selected time dependent signal intensities 526 and one or more selected frequency dependent signal intensities 528 that correspond to one or more impulsive sounds in the audio sequence. An output of the impulsive sound filter 642 may include reduced intensities of the selected signals that correspond to impulsive sounds. In some examples, a fast-acting automatic gain control model may be implemented to reduce sudden impulsive sounds.

The intervention module 640 may further include an overall intensity reduction model 644 to reduce an overall intensity of the audio rendered by the headphones. The overall intensity reduction model 644 may determine a time point when the overall intensity reduction is initiated, the level of intensity reduction, and the duration of intensity reduction based on the level of the incoming audio signal, the level of previous exposure, and the short-term and the long-term risk probabilities.

The intervention module 640 may further include an adaptive spectral shaping model 646 to reduce intensity of acoustic stimuli within selected frequency ranges. Adaptive spectral shaping algorithm works on both the temporal and spectral domains to strategically apply shaping functions across the frequency bands as well as time frames. These spectrogram shaping functions ensure controlled intensity reduction without impacting the audio quality.

The impulsive sound filter 642, the overall intensity reduction model 644, and the adaptive spectral shaping model 646 may be applied to the audio signal input into the SES 110, such as audio signal 113 at FIG. 1, and implemented in addition to the binaural rendering/equalizer system, in order to reduce degradation of hearing to the user/listener utilizing the headphones for listening to the audio.

Taken together, an acoustic evaluation system of a headphone assembly may be utilized to monitor and adjust acoustic stimulation provided by audio rendered to a user actively utilizing the headphone assembly. The acoustic evaluation system may be device-centric, as it takes into account one or more parameters of the transducer driving the headphone assembly. Further, the acoustic evaluation system determines active listener engagement with the headphone to determine active listening status of the listener, and determines probability of short-term risk and probability of long-term risk to the auditory health based on the listening profile of the user, engagement with the headphone assembly, and audio signal input over various durations. Furthermore, the acoustic evaluation system provides one or more indications to the user and provides automatic adjustments to the incoming audio signal to reduce the probability of risk to damage of hearing from short-term and long-term acoustic stimulations.

In some examples, the type of intervention that is applied may be device specific. For example, if the headphones are designed for kids/young adults, the intervention may be applied automatically (e.g., without explicit user input) and the intervention algorithm may be hardcoded into the DSP. In this way, if the short-term risk probability and/or long-term risk probability reaches a respective threshold, an intervention (e.g., impulsive sound filter, overall intensity reduction, and/or adaptive spectral shaping) may be applied automatically. In contrast, a device designed for adults may output an alert/notification and may wait for user confirmation before applying an intervention. Further, the thresholds (short-term load threshold and long term load threshold) for determining when to initiate the intervention may be device specific. For example, a device designed for kids may have lower thresholds than a device designed for adults.

The thresholds may be pre-set by the manufacturer. In some examples, the thresholds may be adjustable by the user, so that the user may set lower thresholds to prevent further auditory risk. The user may adjust the thresholds via the application interface, for example. Additionally or alternatively, more than one short-term threshold and more than one long-term threshold may be applied. For example, when a first, lower short-term threshold is reached, a first intervention may be applied (e.g., outputting an alert/notification). When a second, higher short-term threshold is reached, one or more second interventions may be applied, such as automatically reducing the overall sound intensity. In this way, the user may be given the option to mitigate potential auditory risk when the short-term and/or long-term risks are relatively low (but still potentially risk-inducing) but then when the short-term and/or long-term risks are relatively high, one or more interventions may be automatically applied to mitigate potential auditory risk.

For adult headphones (e.g., gaming headphones), there may be options to make manual adjustments based on feedback provided to the user. Again, the thresholds for intervention may be different for adults. In some examples where audiogram data is available, the threshold for initiating intervention may be based on the audiogram data, and thus the intervention may be user-specific.

While examples are provided herein relating to a dual-channel audio signal, the monitoring, notifications, and/or intervention application described herein may be applied to virtually any type of headphone/speaker, including headphones having more than one driver for an ear to deliver a surround sound experience, headphones delivering a stereo signal, multi-channel/multi-object digital sound format enabled headphones, and/or any other headphone/earphone or over/in-the-ear sound producing device.

The technical effect of adjusting an audio signal and/or acoustic stimulation of a headphone assembly rendering audio to a listener based on monitoring of one or more acoustic profile parameters and monitoring of one or more listener-headphone engagement parameters is the potential mitigation of auditory risk to the listener. By only monitoring when the listener is actually engaged with the headphones (e.g., as opposed to when the headphones are around the listener's neck), the accuracy of the monitoring may be increased.

An embodiment of a method for an audio signal processor, comprises receiving an audio signal from an audio source, receiving headphone position data from a sensor coupled to a headphone assembly rendering the audio signal to a user, receiving one or more transducer parameters from one or more transducers of the headphone assembly, monitoring one or more acoustic profile parameters of the audio signal based on the one or more transducer parameters, monitoring one or more listener-headphone engagement parameters based on the headphone position data, and adjusting the audio signal and/or acoustic stimulation based on the monitoring of the one or more acoustic profile parameters and the monitoring of one or more listener-headphone engagement parameters, wherein the one or more listener-headphone engagement parameters include a current engagement status of the headphone assembly with respect to the user and a duration of active engagement of the headphone assembly with respect to the user. A first example of the method further includes where determining an instantaneous perceived loudness based on the monitoring of the one or more acoustic profile parameters, and wherein the audio signal is adjusted based on the instantaneous perceived loudness and the monitoring of one or more listener-headphone engagement parameters. A second example of the method, optionally including the first example, further includes where determining a short-term acoustic load and a long-term acoustic load based on a perceived loudness profile over a short-term duration of time and an average perceived loudness over a long-term duration respectively; and wherein the audio input signal or output acoustic stimulation is adjusted based on the instantaneous perceived loudness, the short term acoustic load, the long-term acoustic load, and the monitoring of one or more listener-headphone engagement parameters. A third example of the method, optionally including one or more of the previous examples, further includes where a first probability of risk for short-term hearing degradation and a second probability of risk of long-term hearing degradation based on the instantaneous perceived loudness and the short-term acoustic load and the long-term acoustic load respectively, and wherein the audio input signal is adjusted based on the first probability and the second probability. A fourth example of the method, optionally including one or more of the previous examples, further includes where providing one or more indications to the user, via a user interface of the headphone assembly, based on the first probability and the second probability. A fifth example of the method, optionally including one or more of the previous examples, further includes where the one or more indications include one or more of a visual indication, an audible indication, and a haptic indication. A sixth example of the method, optionally including one or more of the previous examples, further includes where adjusting the audio signal includes one or more of filtering impulsive sounds having intensity greater than a threshold intensity, reducing overall intensity of the audio signal, reducing intensity of selected frequencies of the audio signal, and adaptively shaping the sound spectrum over time. A seventh example of the method, optionally including one or more of the previous examples, further includes where the audio signal is a dual-channel audio input signal.

An embodiment of an audio rendering system, comprises a headphone assembly including a headband, a pair of headphones, each including one or more transducers, and one or more sensors coupled to each of the pair of headphones for sensing active headphone engagement with respect to a user, an audio evaluation system for monitoring auditory stimulation provided by an audio input signal rendered to the user via the headphone assembly, the audio evaluation system including a controller with executable instructions stored in non-transitory memory for receiving the audio input signal from an audio source, receiving headphone position data from the one or more sensors, receiving one or more transducer parameters from the headphone assembly, determining a first probability of short-term hearing risk based on the audio input signal, the headphone position data, and the one or more transducer parameters, and adjusting the audio input signal prior to the headphone assembly rendering the audio input signal to the user based on the first probability of short-term hearing risk. A first example of the audio rendering system further includes where the controller is communicatively coupled to a user interface having a display portion; and wherein the controller includes further instructions for visually indicating, via the display portion, an auditory stimulation status of the user based on the first probability of short-term hearing risk. A second example of the audio rendering system, optionally including the first example, further includes where the headphone assembly includes the user interface. A third example of the audio rendering system, optionally including one or more of the previous examples, further includes where the user interface is part of a computing device. A fourth example of the audio rendering system, optionally including one or more of the previous examples, further includes where the one or more sensors providing headphone position data include position sensors. A fifth example of the audio rendering system, optionally including one or more of the previous examples, further includes where the instructions enable the controller to determine if the user is listening with both the pair of headphones or only one of the pair of headphones. A sixth example of the audio rendering system, optionally including one or more of the previous examples, further includes where the instructions enable the controller to monitor a duration of engagement between one or both the pair of headphones and an ear or ears of the user.

A system, comprises a headphone assembly including a headband coupled to a pair of headphones at opposite extreme ends, wherein each of the pair of headphones includes one or more transducers, and one or more sensors coupled to each of the pair of headphones for sensing active headphone engagement with respect to a user, and a controller comprising computer-readable instructions stored on non-transitory memory thereof that when executed enable the controller to determine a position of each of the pair of headphones relative to a left ear and a right ear of the user, and monitor a duration of headphone engagement with the left ear, the right ear, or both ears in response to the position of each of the pair of headphones. A first example of the system further includes where the instructions further enable the controller to determine a short term risk probability and a long term risk probability of degradation to the left ear and the right ear based on one or more of the duration, an instantaneous perceived loudness, a short-term acoustic load profile, an average long-term acoustic load, a time dependent signal intensity, and an instantaneous frequency dependent signal intensity. A second example of the system, optionally including the first example, further includes where the pair of headphones comprise a display portion, wherein the instructions further enable the controller to provide one or more indications to the user via the display portion based on the short term risk probability and the long term risk probability. A third example of the system, optionally including one or more of the previous examples, further includes where the instructions further enable the controller to adjust an audio signal, wherein the audio signal includes one or more of filtering impulsive sounds having intensity greater than a threshold intensity, reducing overall intensity of the audio signal, reducing intensity of selected frequencies of the audio signal, and adaptively shaping the sound spectrum over time, wherein the audio signal is adjusted in response to the short term risk probability reaching a short term threshold or the long term risk probability reaching a long term threshold. A fourth example of the system, optionally including one or more of the previous examples, further includes where the pair of headphones are positioned on top of the left and right ears, surrounding the left and right ears, or within the left and right ears.

Note that the example control and estimation routines included herein can be used with various audio processing system configurations. The control methods and routines disclosed herein may be stored as executable instructions in non-transitory memory and may be carried out by the control system including the controller in combination with the various sensors, actuators, and other hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the control system, where the described actions are carried out by executing the instructions in a system including the various hardware components in combination with the electronic controller.

It will be appreciated that the configurations and routines disclosed herein are exemplary in nature, and that these specific embodiments are not to be considered in a limiting sense, because numerous variations are possible. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method for an audio signal processor, comprising:
receiving an audio signal from an audio source;
receiving headphone position data from a sensor coupled to a headphone assembly rendering the audio signal to a user;
receiving head position data from a second sensor coupled to the headphone assembly rendering the audio signal to the user;
receiving one or more transducer parameters from one or more transducers of the headphone assembly;
monitoring one or more acoustic profile parameters of the audio signal based on the one or more transducer parameters;
monitoring one or more listener-headphone engagement parameters based on the headphone position data; and
adjusting the audio signal and/or acoustic stimulation based on the monitoring of the one or more acoustic profile parameters, the monitoring of one or more listener-headphone engagement parameters, and the head position data; and
determining an instantaneous perceived loudness based on the monitoring of the one or more acoustic profile parameters, wherein the audio signal is adjusted based on the instantaneous perceived loudness and the monitoring of the one or more listener-headphone engagement parameters;
wherein the one or more listener-headphone engagement parameters include a current engagement status of the headphone assembly with respect to the user and a duration of active engagement of the headphone assembly with respect to the user;
wherein adjusting the audio signal includes one or more of filtering impulsive sounds having an intensity greater than a threshold intensity, reducing an overall intensity of the audio signal, reducing an intensity of selected frequencies of the audio signal, and adaptively shaping a sound spectrum over time, and wherein the one or more acoustic profile parameters of the audio signal are generated from the one or more transducer parameters and further based on extracting features from the audio signal, including temporal features, spectral features, and overall frequency-dependent intensity levels.

2. The method of claim 1, further comprising determining a short-term acoustic load and a long-term acoustic load based on a perceived loudness profile over a short-term duration of time and an average perceived loudness over a long-term duration, respectively, wherein an audio input signal or an output acoustic stimulation is adjusted based on the instantaneous perceived loudness, the short-term acoustic load, the long-term acoustic load, and the monitoring of the one or more listener-headphone engagement parameters.

3. The method of claim 2, further comprising determining a first probability of risk for short-term hearing degradation and a second probability of risk of long-term hearing degradation based on the instantaneous perceived loudness and the short-term acoustic load and the long-term acoustic load, respectively, wherein the audio input signal is adjusted based on the first probability and the second probability.

4. The method of claim 3, further comprising providing one or more indications to the user, via a user interface of the headphone assembly, based on the first probability and the second probability.

5. The method of claim 4, wherein the one or more indications include one or more of a visual indication, an audible indication, and a haptic indication.

6. The method of claim 1, wherein the audio signal is a dual-channel audio input signal, the acoustic profile parameters further based on audiogram parameters of the user.

7. An audio rendering system, comprising:
a headphone assembly including a headband, a pair of headphones, each including one or more transducers, and one or more sensors coupled to each of the pair of headphones for sensing active headphone engagement with respect to a user; and
an audio evaluation system for monitoring auditory stimulation provided by an audio input signal rendered to the user via the headphone assembly, the audio evaluation system including:
a controller with executable instructions stored in non-transitory memory for:
receiving the audio input signal from an audio source;
receiving headphone position data from the one or more sensors;
receiving one or more transducer parameters from the headphone assembly;
receiving one or more acoustic profile parameters of the audio input signal, wherein the one or more acoustic profile parameters of the audio input signal are generated from the one or more transducer parameters, wherein the one or more acoustic profile parameters are further based on extracting features from the audio input signal, including temporal features, spectral features, and overall frequency-dependent intensity levels, and wherein the one or more acoustic profile parameters are further based on audiogram parameters of the user;
determining a first probability of short-term hearing risk based on the one or more acoustic profile parameters and the headphone position data; and
adjusting the audio input signal prior to the headphone assembly rendering the audio input signal to the user based on the first probability of short-term hearing risk.

8. The audio rendering system of claim 7, wherein the controller is communicatively coupled to a user interface having a display portion, and wherein the controller includes further instructions for visually indicating, via the display portion, an auditory stimulation status of the user based on the first probability of short-term hearing risk.

9. The audio rendering system of claim 7, wherein the headphone assembly includes a user interface.

10. The audio rendering system of claim 9, wherein the user interface is part of a computing device.

11. The audio rendering system of claim 7, wherein the one or more sensors providing headphone position data include position sensors.

12. The audio rendering system of claim 11, wherein the instructions enable the controller to determine if the user is listening with both the pair of headphones or only one of the pair of headphones.

13. The audio rendering system of claim 12, wherein the instructions enable the controller to monitor a duration of engagement between one or both of the pair of headphones and an ear or ears of the user.

14. A system, comprising:
   a headphone assembly including a headband coupled to a pair of headphones at opposite extreme ends, wherein each of the pair of headphones includes one or more transducers, and one or more sensors coupled to each of the pair of headphones for sensing active headphone engagement with respect to a user; and
   a controller comprising computer-readable instructions stored on non-transitory memory thereof that when executed enable the controller to:
      determine current engagement via identification of a position of each of the pair of headphones relative to a left ear and a right ear of the user;
      monitor a duration of headphone engagement with the left ear, the right ear, or both ears in response to the position of each of the pair of headphones;
      output the current engagement and the duration;
      determine via machine learning a short-term risk probability and a long-term risk probability of degradation to the left ear and the right ear based on one or more of the current engagement and the duration; and
      adjust an audio signal based on one or more of the short-term risk probability and the long-term risk probability.

15. The system of claim 14, wherein the short-term risk probability and the long-term risk probability of degradation to the left ear and the right ear are based on one or more of the duration, an instantaneous perceived loudness, a short-term acoustic load profile, an average long-term acoustic load, a time-dependent signal intensity, and an instantaneous frequency-dependent signal intensity.

16. The system of claim 15, wherein the pair of headphones comprises a display portion, wherein the instructions further enable the controller to provide one or more indications to the user via the display portion based on the short-term risk probability and the long-term risk probability.

17. The system of claim 16, wherein adjusting the audio signal includes one or more of filtering impulsive sounds having an intensity greater than a threshold intensity, reducing an overall intensity of the audio signal, reducing an intensity of selected frequencies of the audio signal, and adaptively shaping a sound spectrum over time, and wherein the audio signal is adjusted in response to the short-term risk probability reaching a short-term threshold or the long-term risk probability reaching a long-term threshold.

18. The system of claim 14, wherein the pair of headphones are positioned on top of the left and right ears, surrounding the left and right ears, or within the left and right ears.

* * * * *